United States Patent
Schmidt et al.

(10) Patent No.: US 9,488,554 B2
(45) Date of Patent: Nov. 8, 2016

(54) METHOD AND SYSTEM FOR REDUCING CURTAINING IN CHARGED PARTICLE BEAM SAMPLE PREPARATION

(71) Applicant: FEI Company, Hillsboro, OR (US)

(72) Inventors: Michael Schmidt, Gresham, OR (US); Hyun Hwa Kim, Seoul (KR); Sang Hoon Lee, Hillsboro, OR (US); Stacey Stone, Portland, OR (US); Jeffrey Blackwood, Portland, OR (US)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 14/432,711

(22) PCT Filed: Oct. 7, 2013

(86) PCT No.: PCT/US2013/063640
§ 371 (c)(1),
(2) Date: Mar. 31, 2015

(87) PCT Pub. No.: WO2014/055974
PCT Pub. Date: Apr. 10, 2014

(65) Prior Publication Data
US 2015/0276567 A1    Oct. 1, 2015

Related U.S. Application Data

(60) Provisional application No. 61/710,458, filed on Oct. 5, 2012, provisional application No. 61/748,029, filed on Dec. 31, 2012.

(51) Int. Cl.
*H01J 37/00*    (2006.01)
*G01N 1/32*    (2006.01)
(Continued)

(52) U.S. Cl.
CPC ............ *G01N 1/32* (2013.01); *G01N 1/286* (2013.01); *H01J 37/20* (2013.01); *H01J 37/3053* (2013.01); *H01J 2237/31745* (2013.01)

(58) Field of Classification Search
USPC .............................. 250/492.1, 492.2, 492.3
See application file for complete search history.

(56) References Cited

U.S. PATENT DOCUMENTS 5,435,850 A    7/1995  Rasmussen
5,851,413 A   12/1998  Casella et al.
(Continued)

OTHER PUBLICATIONS

H.B. Chong et al., "Sideways FIB TEM Sample Preparation for Improved Construction Analysis in TEM", 2012 19th IEEE International Symposium on the Physical and Failure Analysis of Integrated Circuits (IPFA), Jul. 2, 2012, 4 pages.
(Continued)

*Primary Examiner* — Nicole Ippolito
*Assistant Examiner* — Hanway Chang
(74) *Attorney, Agent, or Firm* — Scheinberg & Associates, P.C.; Michael O. Scheinberg; John B. Kelly

(57) ABSTRACT

A method and system for exposing a portion of a structure in a sample for observation in a charged particle beam system, including extracting a sample from a bulk sample; determining an orientation of the sample that reduces curtaining; mounting the sample to a holder in the charged particle beam system so that the holder orients the sample in an orientation that reduces curtaining when the sample is milled to expose the structure; exposing the structure by milling the sample in a direction that reduces curtaining; and imaging the structure.

19 Claims, 15 Drawing Sheets

(51) Int. Cl.
*G01N 1/28* (2006.01)
*H01J 37/20* (2006.01)
*H01J 37/305* (2006.01)

(56) References Cited

U.S. PATENT DOCUMENTS

| | | |
|---|---|---|
| 8,822,921 B2 | 9/2014 | Schmidt et al. |
| 8,859,963 B2 | 10/2014 | Moriarty et al. |
| 8,859,998 B2 | 10/2014 | Blackwood et al. |
| 8,912,490 B2 | 12/2014 | Kelley et al. |
| 2002/0088947 A1 | 7/2002 | Moran |
| 2002/0170675 A1 | 11/2002 | Libby et al. |
| 2005/0118065 A1 | 6/2005 | Hasegawa et al. |
| 2010/0108506 A1 | 5/2010 | Nadeau et al. |
| 2013/0186747 A1 | 7/2013 | Schmidt et al. |
| 2013/0240353 A1 | 9/2013 | Watanabe et al. |
| 2013/0248354 A1 | 9/2013 | Keady et al. |
| 2013/0328246 A1 | 12/2013 | Wells et al. |
| 2015/0243477 A1 | 8/2015 | Stone et al. |
| 2015/0243478 A1 | 8/2015 | Lee et al. |

OTHER PUBLICATIONS

H. Bender et al., "FIB/SEM Structural Analysis of Through-Silicon-Vias", AIP Conference Proceedings, Jan. 1, 2011, 6 pages.

"Methods for Low Curtaining HAR via Metrology and Characterization", ip.com Journal, ip.com Inc., Aug. 7, 2013, 1 page.

Material Removed →

METHOD AND SYSTEM FOR REDUCING CURTAINING IN CHARGED PARTICLE BEAM SAMPLE PREPARATION

TECHNICAL FIELD OF THE INVENTION

The present invention relates to charged particle beam processing.

BACKGROUND OF THE INVENTION

Structures forming integrated circuits and other nanotechnology have dimensions on the nanometer scale. One method of observing the structures for purposes such as process development, process control, and defect analysis is to expose a portion of the structure using a focused ion beam (FIB) system and observing the exposed structure using a scanning electron microscope (SEM) or a transmission electron microscope (TEM). When the ion beam mills material to expose a structure for observation, the ion beam can distort the structure and create artifacts that interfere with the observation.

A high aspect ratio (HAR) structure is a structure having a dimension, such as height, that is much greater than another dimension, such as its width. For example, a hole between layers in an integrated circuit may have a height that is several times greater than its width. For example, a feature having a height more than 3 times its width.

In analyzing high aspect ratio structures, especially unfilled contacts or vias, for the 3D structures in integrated circuits, such as 3D NAND circuits used in flash memory, the conventional ion beam sample preparation process causes artifacts, such as structure distortion, and the ion beam curtain effect.

The ion beam curtain effect or curtaining occurs when material is removed at different milling rates. This can happen when milling a feature comprised of materials that are removed at different rates by the same beam. This can also happen when milling a surface that has an irregular shape. For example, the feature of interest can be a through-silicon vias (TSV). Cross-sectioning TSVs is a common practice in semiconductor labs to characterize voids and surface interfaces. Due to the depth of TSVs (typically 50-300 nm), milling a cross section of a TSV with an ion beam can result in substantial curtaining.

Because of the damage and artifacts caused by the ion beam milling to expose the features, the images do not faithfully show the results of the fabrication process and interfere with measurements and with an assessment of the fabrication process since the image and measurements show the results of the sample preparation and not the manufacturing process. It also makes performing high aspect ratio vertical structure analysis difficult.

Producing curtain-less TEM samples of 3D NAND and other IC structures w/recurrent high aspect ratio holes such as vias or contacts is currently difficult or non-achievable. It has been difficult or impossible to retain shape integrity of high aspect ratio holes or trenches when milling or preparing with a FIB and/or imaging with a SEM. When there are unfilled holes on a sample there are high differentials in the milling rates between the material and areas adjacent to the open area (hole). The large difference in milling rates results in curtaining or water fall effects that distort the shape of the hole.

The FIB produces artifacts on open structures. Etched holes or trenches when processed for cross sections to TEM prep with a FIB are prone to severe curtaining artifacts. Making interpretation of the cross section or difficult or impossible. High aspect ratio holes or trenches with complex material stacks are difficult measure with other methods (scatterometry, CD-SEM, etc.) Plan view or glancing angle material removal allows access to various depths for measurement. However, such methods do not provide a view from an electron beam that is normal along the entire length of a high aspect ratio hole or via.

In the prior art, curtaining effects are mitigated by placing protective depositions across the top surface of the sample or by doing the highest offset angle mill possible given the sample geometry, even to the point of inverting the sample. The ability to re-orient a work piece such as a semiconductor wafer in a vacuum chamber of a FIB is typically limited. Gaining milling and viewing capabilities from multiple planes of a sample also presents a number of problems. Prior art techniques for manipulating a sample in a charged particle beam system are very limited, typically only allowing one or two planes of viewing. Current methods of chunking and welding can only provide limited information due to system hardware constraints. Lengthy time periods are required to make multiple welds and multiple sample manipulations. Manually loading and unloading the sample from system, flipping the sample, or placing the sample in a different holder can be required, further increasing processing time. Other methods include slicing through a region of interest in one plane and then reconstructing data to get information from other angles. This method is time consuming, however, requires forming a number of images after multiple mills and then reconstructing the data to form an image in a different plane.

What is needed is a way to expose regions of interest for examination and/or measurement and produce an accurate image that reflects the region of interest without damaging the region or creating artifacts in the exposed surface. What is also needed is an improvement over prior art milling and viewing capabilities from multiple planes of a sample.

SUMMARY OF THE INVENTION

Embodiments of the present invention are directed to samples having reduced damage and artifacts in structures, such as high aspect ratio holes, formed by FIB milling for viewing on an SEM, TEM, or other device.

In some embodiments, a sample is analyzed to determine a milling orientation that will reduce artifacts. The sample is reoriented prior to milling so that it can be milled from a direction that reduces artifacts. Either an extracted sample or an entire work piece can be oriented to reduce artifacts.

Embodiments of the invention optimize an ion beam milling angle to reduce artifacts such as curtaining. Some embodiments extract a portion from the work piece. The extracted portion can be re-oriented before ion beam milling so that the portion is milled from a direction that reduces curtaining and other artifacts. The extracted portion can be mounted onto a holder. The holder is preferably rotatable, so that the sample can be milled from a direction that reduces artifacts and then can be viewed from an optimum direction, preferably by an electron beam normal to the surface.

Some embodiments allow the ion beam to expose cross sections that could not be exposed while the portion was still part of the larger work piece, and allows the sample to be milled from directions that would not be otherwise accessible. For example, the entire length of a hole can be exposed in cross section for viewing by an SEM at 90 degrees in a dual beam system. In some embodiments, the extracted portion is moved from the work piece using a micromanipulator and is then attached to a holder that is preferably rotatable. In some embodiments, the extracted portion is reoriented for milling and/or viewing directly on the micromanipulator.

An embodiment of the present invention is directed to extracting single small volume chunk containing the multiple regions of interest. The extracted chunk is mounted to holder (TEM grid, for example) that is supported on a stage or other holder that provides independent motion control.

The larger sample volume can then be sliced into small chunks that can then be re-mounted in multiple planes so further preparation methods can be used for analysis.

Plan view and normal TEM prep extracted from single piece. Multiple angles and sides can be viewed 360 degrees around. Pieces can also be removed, and regular cross sections performed and then viewed at short working distance and 90 degrees to the E beam for high resolution, then prepped for TEM if needed.

Embodiments of the present invention include a motion stage disposed on a bulk sample stage. The bulk sample stage translates in the x-axis and the y-axis. The motion stage translates in the z-axis and includes a sample holder that rotates about its axis. A single sample chunk having multiple regions of interest can be extracted using a first holder and transferred to the sample holder on the motion stage. Once on the motion stage, the sample chunk is oriented using the bulk sample stage and the motion stage so that the region of interest can be viewed and milled to expose a feature in the region of interest.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

During ion beam milling to expose the interior of a sample for observation, variation in structural density can introduce non-planarity and topographical artifacts in the final FIB milled face. This is particularly problematic in the preparation of TEM samples where two cross-sectional faces are milled in close proximity, resulting in a thin film of the sample. By milling the cross-sectional face from a direction not perfectly normal to the sample surface these "curtaining" effects can be directed parallel to the beam direction. On a sample with repeating structures of varying density the direction of the "curtains" can be aliased across multiple repeating structures, in effect reducing or eliminating the curtaining.

Figure 1:
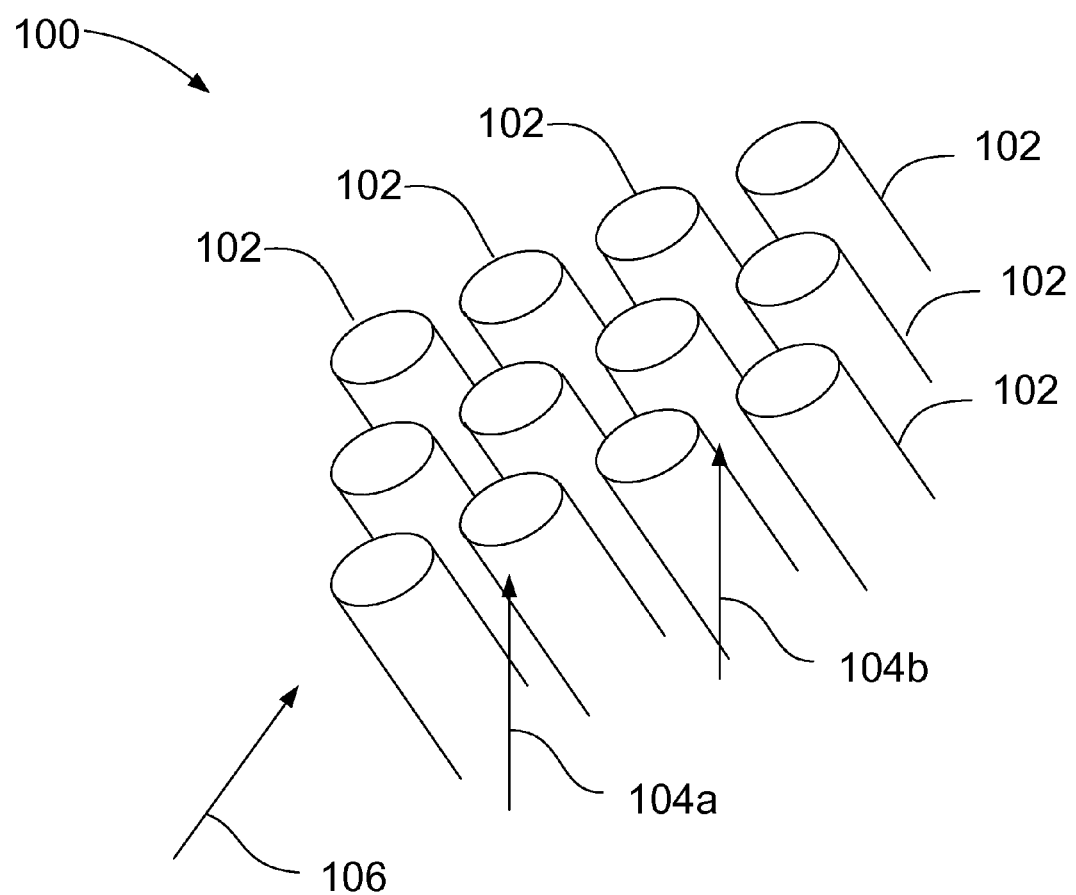
FIG. 1 shows a sample having high aspect ratio features.

FIG. 1 shows a portion of a work piece 100 having multiple high aspect ratio structures, such as holes 102. When an ion beam is oriented to the work piece as shown by arrows 104a and 104b, the exposed cross section will show severe curtaining. During part of the ion beam scan, when the beam is positioned as shown by arrow 104a, the beam crosses multiple holes 102. During a part of the scan as shown by arrow 104b, the beam does not cross any holes. The inconsistency leading to severe curtaining.

Figure 8A:
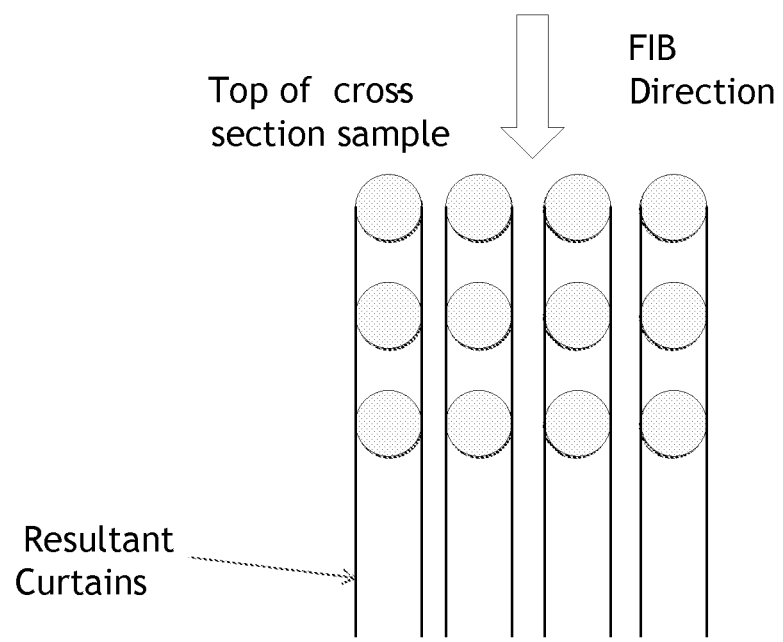
FIG. 8A shows a diagram of a sample cross section that suffers from curtaining effects.
Figure 8B:
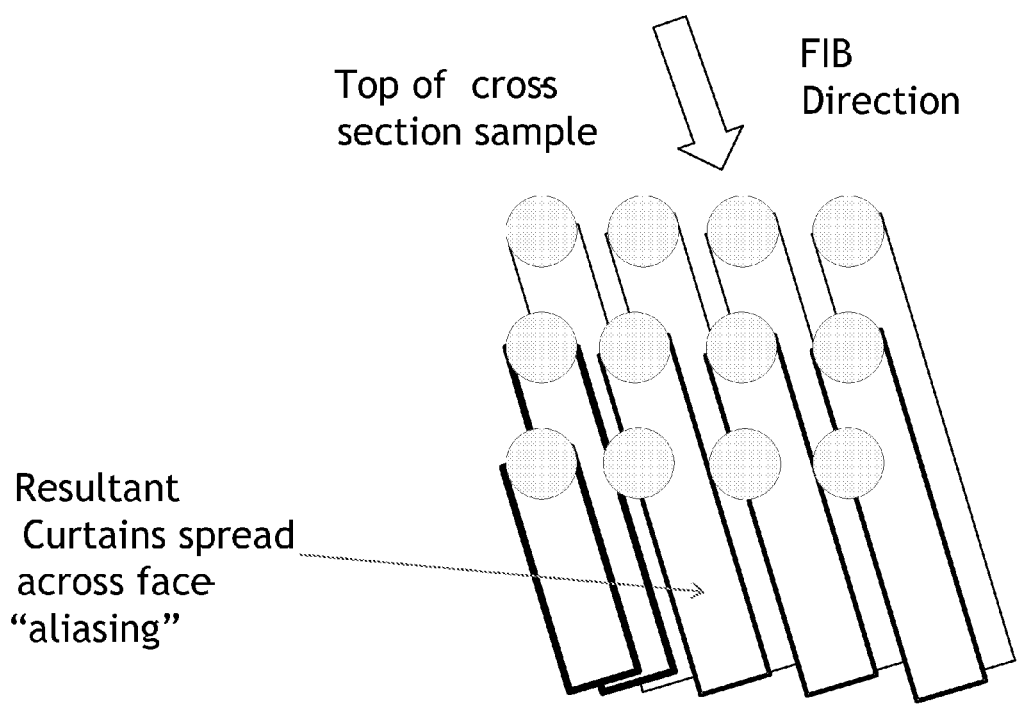
FIG. 8B shows a diagram of a sample cross section with reduced curtaining effects in accordance with embodiments of the present invention.

When the ion beam is oriented as shown by arrow 106, the beam will encounter a combination of holes and solid regions throughout the scan. This reduces curtaining because the beam encounters similar conditions at all positions of the scan. The effect of the sample orientation on curtaining is also shown in FIGS. 8A, 8B, and 8C.

In some embodiments, a beam orientation is calculated to present to the beam the most consistent conditions along the beam scan. For example, a plane may be calculated that maximizes the area of projection of the holes 102 onto the plane. The beam is then oriented normal to the calculated plane to produce a cross section with reduced curtaining. Other algorithms can be used to determine preferred or optimum milling orientation.

Some embodiments of the invention use sample geometry information to determine the offset angle precisely. By analyzing the sample geometry one can implement milling strategies that improve throughput and reliability of a process. This optimization may be applied to most varying-density structures, including cross-sectional sample creation and TEM sample preparation.

Some embodiments involve identifying the optimum angle offset from normal incidence to mill a cross-sectional face based on the geometry of the repeating varying-density structures in the sample. This is particularly effective in semiconductor samples. The invention consists of identifying the varying-density structures that will cause problematic curtaining effects, analyzing the geometry of the structures, and offsetting the milling angle to optimize the aliasing effects of spreading the curtains across the structures. Thus, one can first determine and optimum orientation of the ion beam to maximize the uniformity of beam path through the sample throughout the beam scan. Then, the sample or beam is oriented to impact the sample at the determined angle. After the sample is milled, the exposed surface is viewed with an SEM or TEM.

Figure 2:
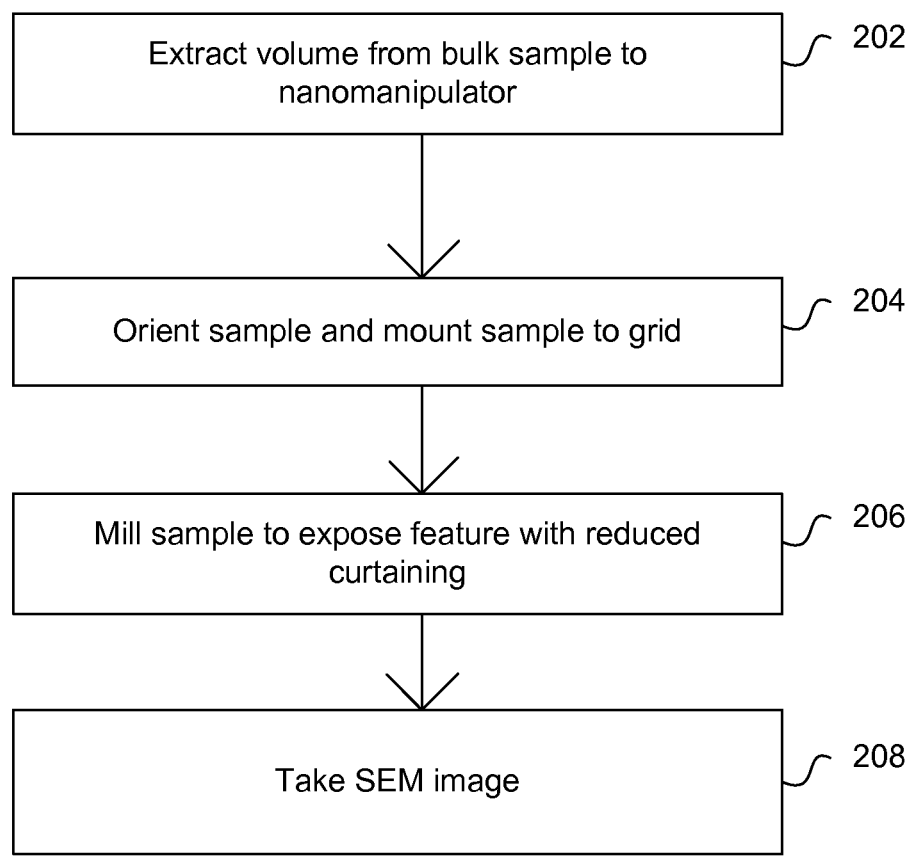
FIG. 2 shows a general process flow of a preferred embodiment of the invention in which a volume is extracted from a sample to a nanomanipulator, mounted to a grid, repositioned, and milled before an SEM image is taken of the volume.
Figure 3A:
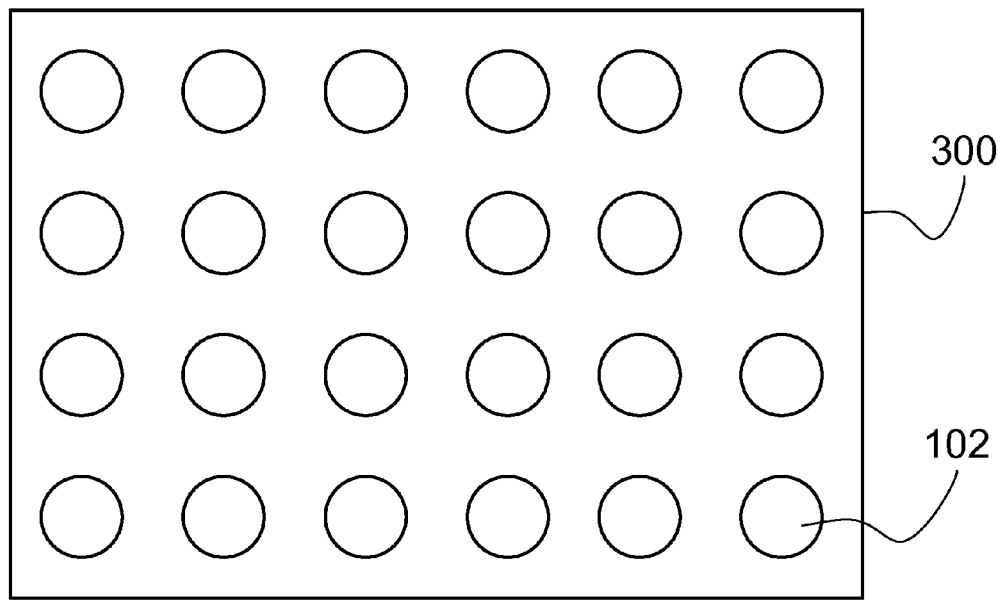
FIG. 3A shows the top down view of a sample.
Figure 3B:
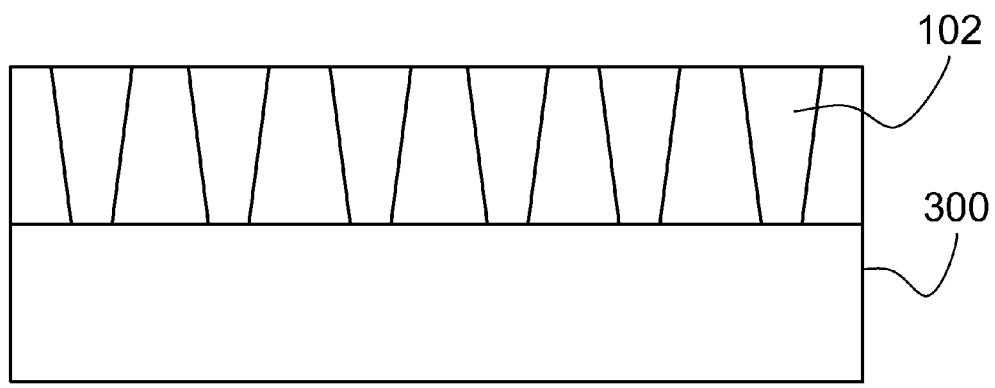
FIG. 3B shows the side view of a sample.
Figure 4:
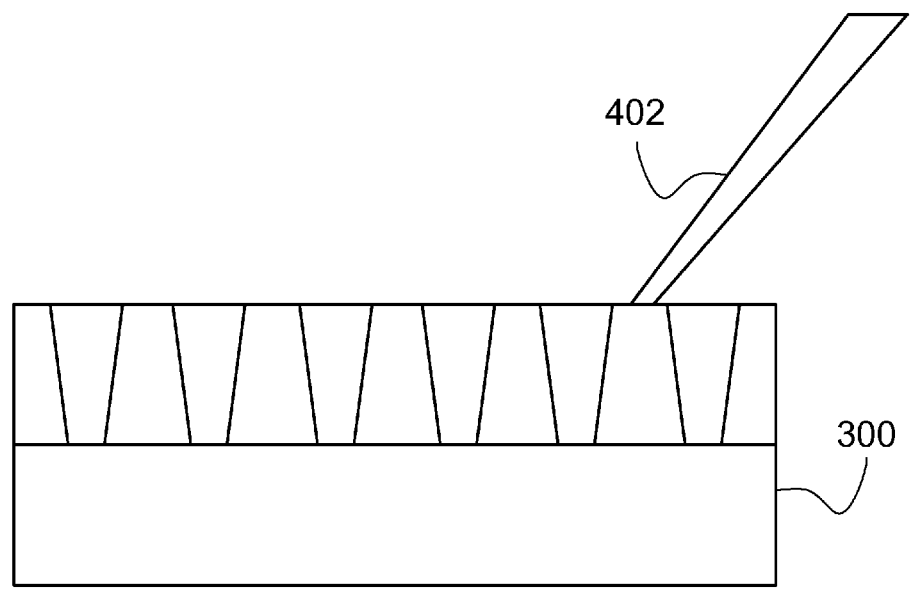
FIG. 4 shows a sample attached to a nanomanipulator following extraction from the work piece.

The steps of another embodiment of the present invention shown in FIG. 2. In step 202, a sample is extracted from a work piece using a nanomanipulator 402, depicted in FIG. 4. FIG. 4 shows a sample attached to nanomanipulator 402 following extraction from the work piece. FIG. 3A shows a top view of a sample 300. FIG. 3B shows a top view of a sample 300.

Figure 5:
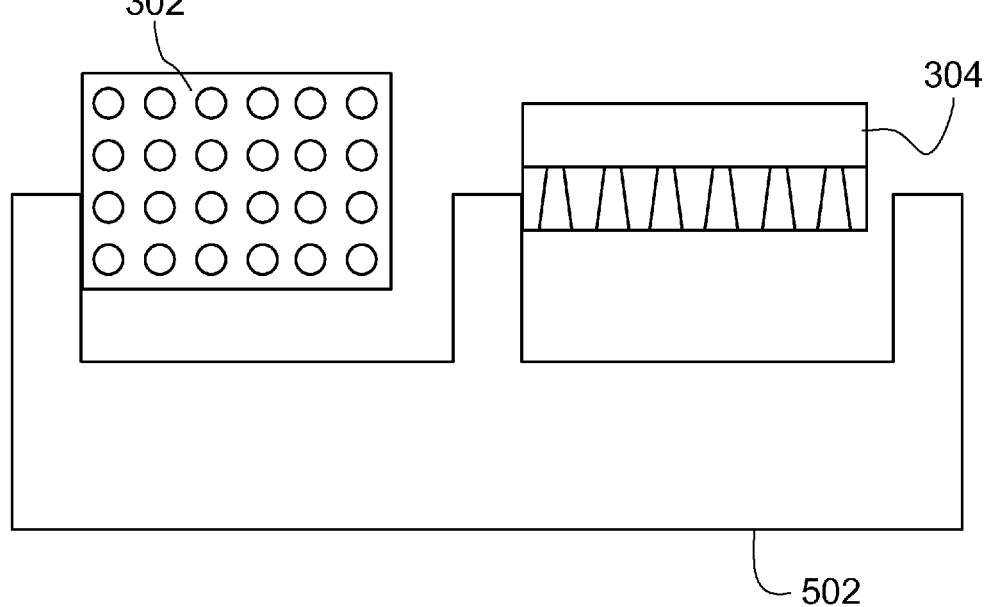
FIG. 5 shows a sample attached to a holder, such as grid 502.
Figure 6A:
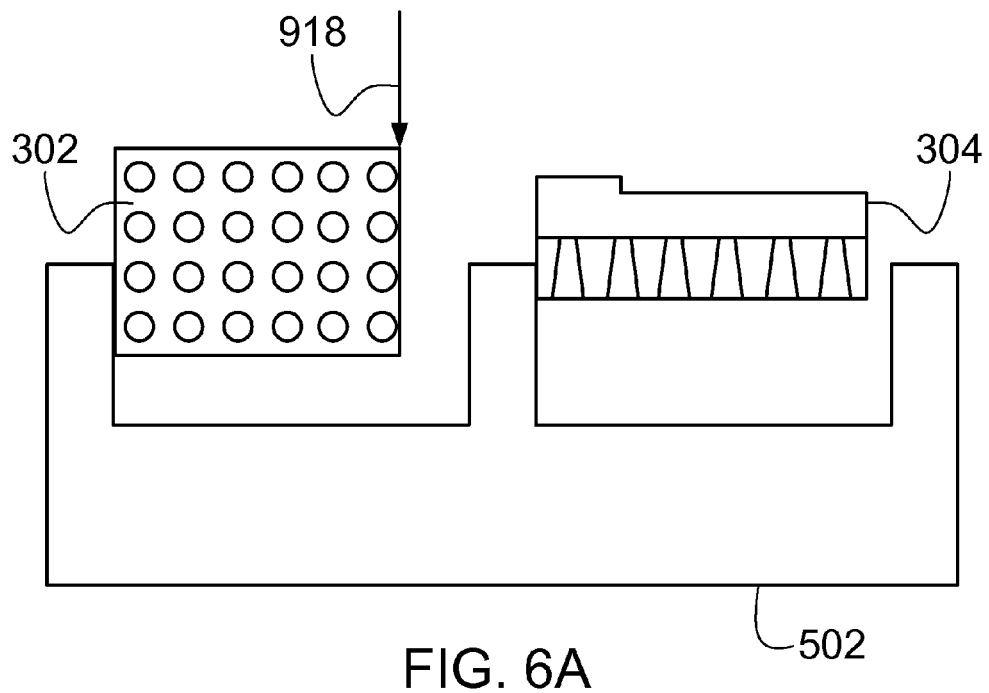
FIGS. 6A-6F show a method of mounting and milling a sample to provide for characterizing a hole over its entire cross section in cross section.
Figure 6B:
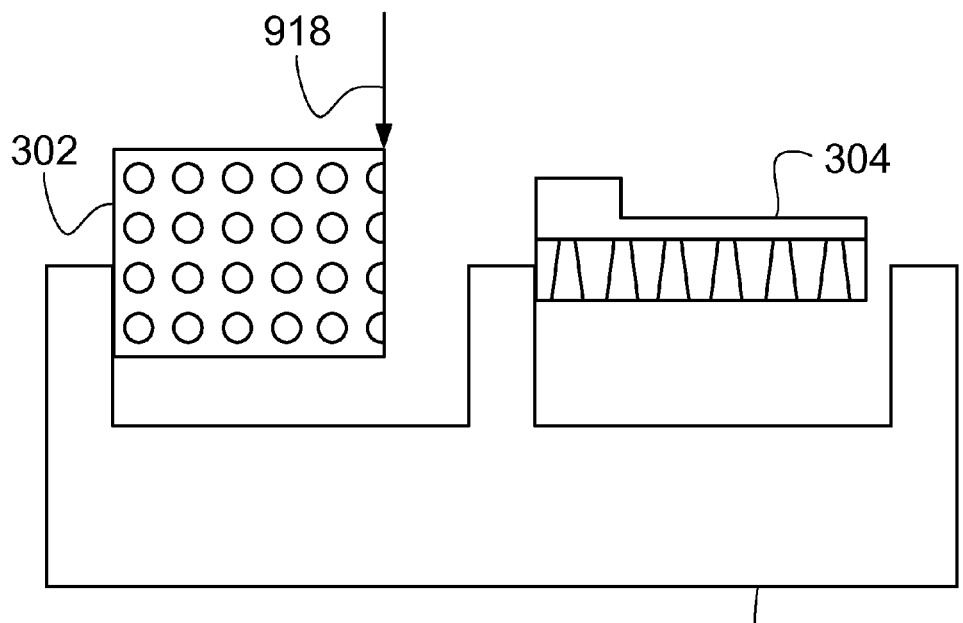
Figure 6C:
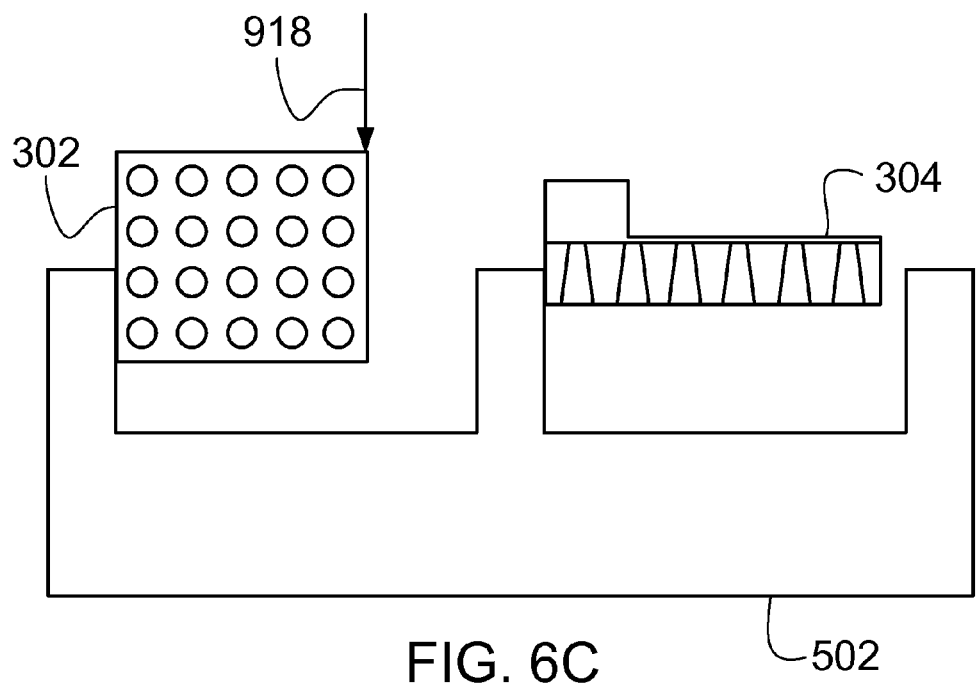
Figure 6D:
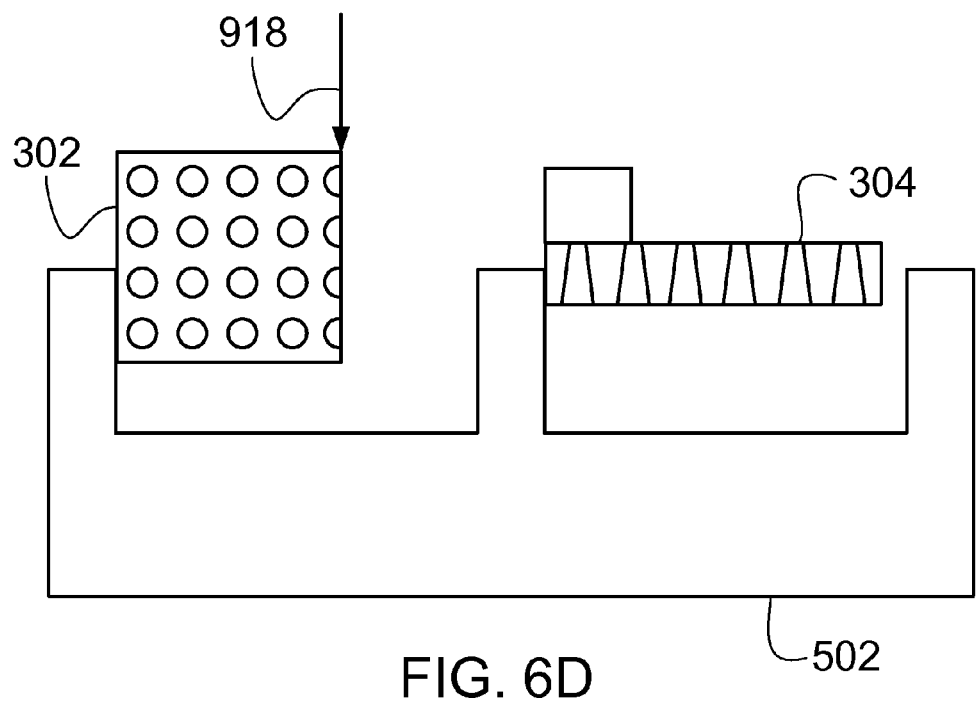
Figure 6E:
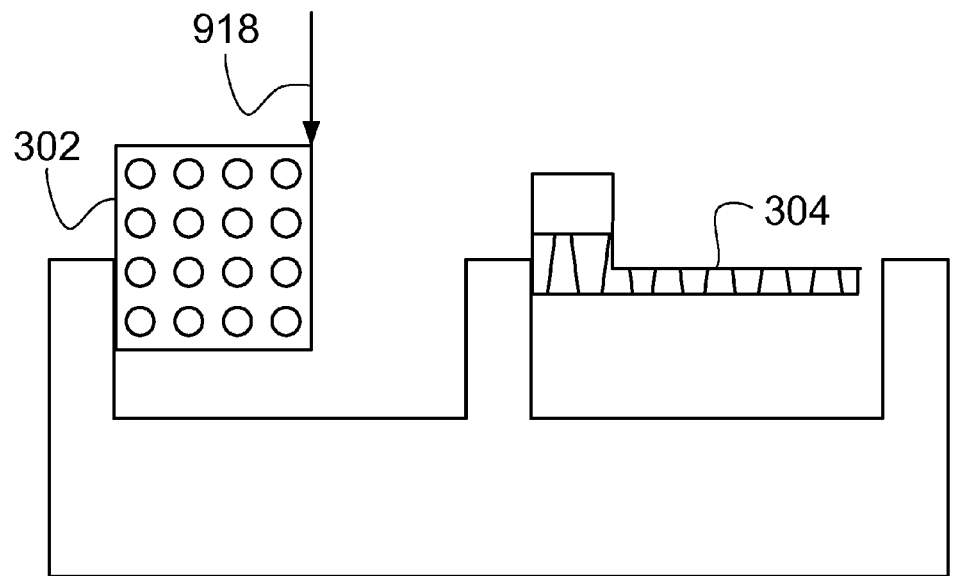
Figure 6F:
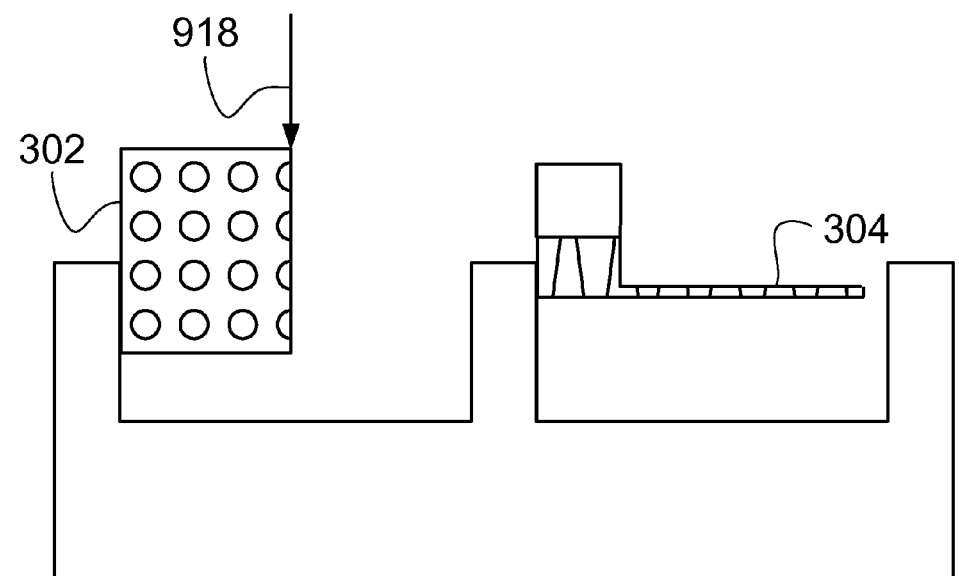
Figure 7A:
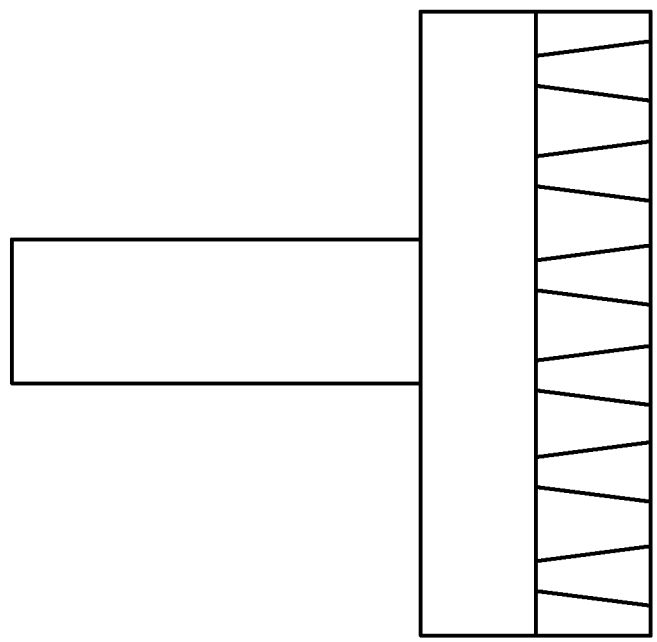
FIGS. 7A-7E show another method of mounting and milling a sample to provide for characterizing a hole over its entire cross section in cross section.
Figure 7B:
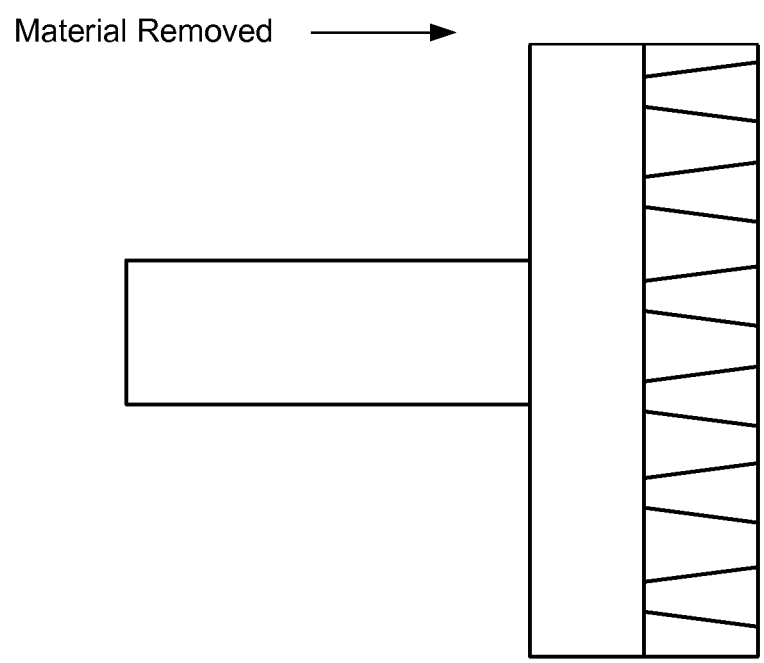
Figure 7C:
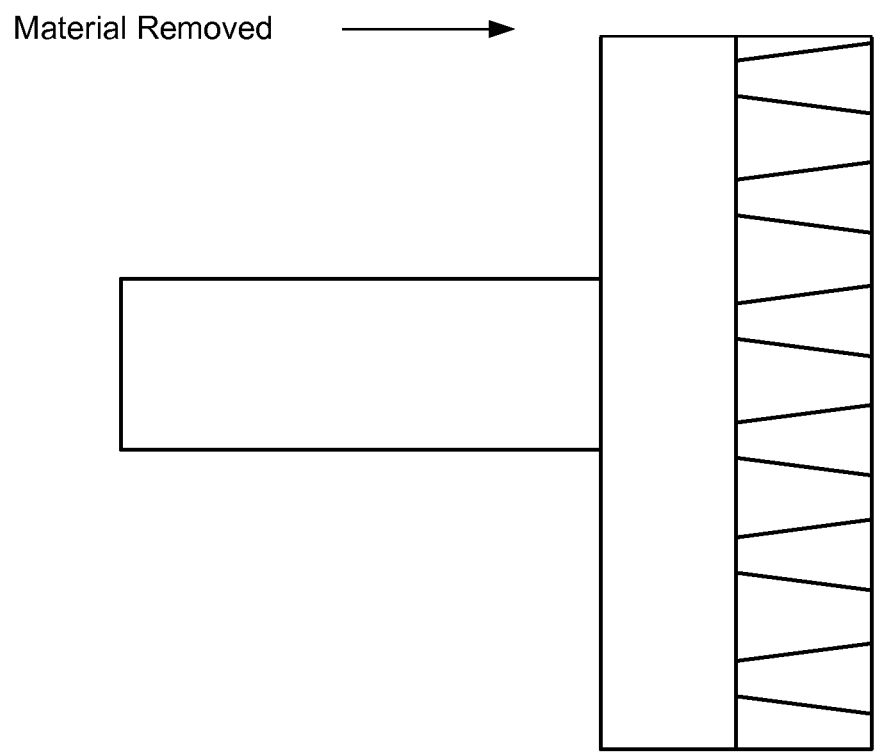
Figure 7D:
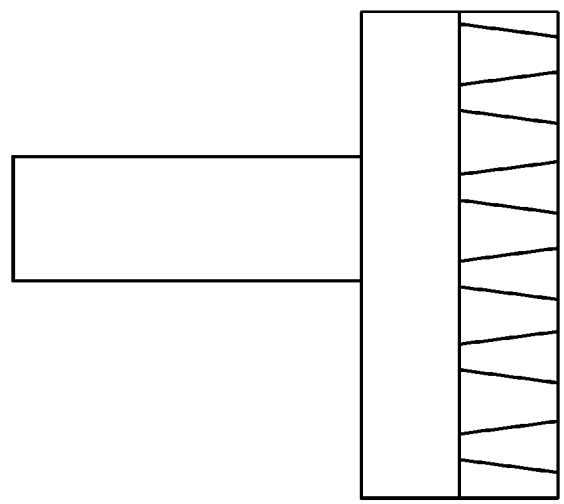
Figure 7E:
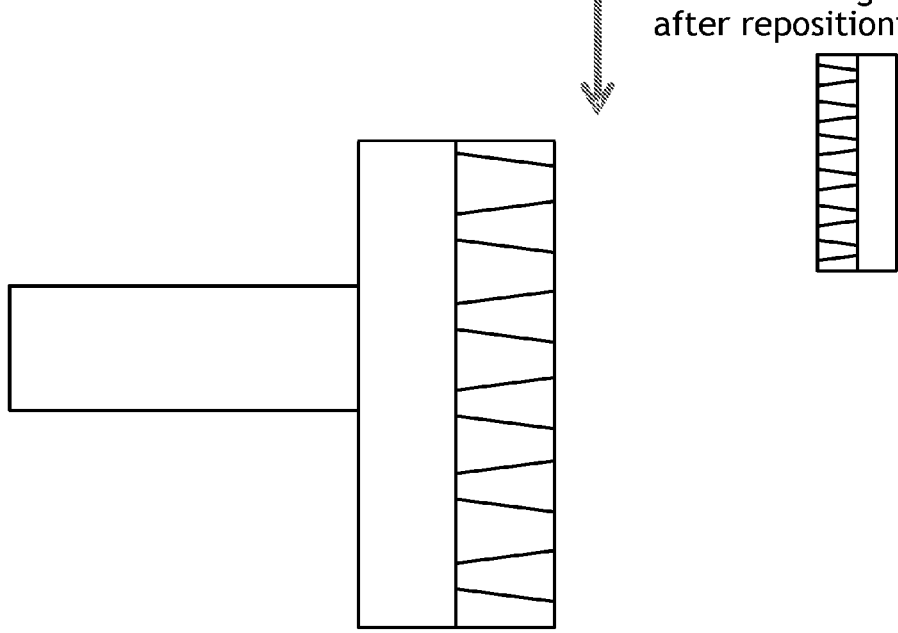

In step 204, the sample is oriented and attached to a holder, such as grid 502 (FIG. 5), typically using ion beam-induced deposition. FIG. 5 shows two samples containing the same structure attached to the grid 502 in two different orientations. The two different orientations allow features of the sample 302 and 304 to be exposed in different ways for analysis and preferably reduce curtaining. For example, as described in further detail below, the orientation of sample 302 provides for characterizing the full depth of the high aspect ratio interconnect with minimal curtaining. The orientation of sample 304 provides for viewing a cross section of the holes at a particular depth. In some embodiments, the grid is rotatable so that sample 302 can be milled from above as shown in FIG. 6A and, by rotating the grid, sample 304 can be milled into the page as shown in FIG. 6B. Sample 302 and sample 304 are each milled to an increasing degree from FIG. 6A to FIG. 6F, such that the least amount of milling is shown in FIG. 6A and the most amount of milling is shown in FIG. 6F. The amount of milling shown in FIGS. 6A-6F is only exemplary, and more or less milling can be performed. After the sample is milled as shown, for example, in FIGS. 6A-6E, the holes of sample 302 can be characterized over their complete depth by taking an SEM image of the hole cross sections as shown in FIG. 6f. Sample 304 allows multiple hole cross sections at a specific depth to be viewed and measured. After reorienting the grid 502, the milled surface of sample 304 can be oriented normal to an SEM in a dual beam system.

FIGS. 7A-7E show another method of mounting a sample to provide for characterizing a hole over its entire cross section in cross section. A sequence of mills shows the sample being milled staring at FIG. 7A until the cross section of a hole is exposed for viewing in FIG. 7E. In some embodiments, multiple samples can be separately extracted and attached to the grid. In some embodiments, one sample can be extracted and attached to the grid, and then divided into additional samples which are then attached to different points on the grid. The orientation of the sample can be determined as described above to minimize curtaining. Some embodiments of the invention can accomplish the following:

Full depth cross section of HAR interconnect that can be viewed at 90 degrees to SEM with minimal curtaining;
90 degree to SEM viewing of interconnect hole from the top to the bottom with minimal curtaining, also allowing vertical 3D reconstruction of the hole; and
True flat surface viewing of the sample.

FIG. 8A shows a diagram of a sample cross section that suffers from curtaining effects. In this example, the cross section was milled in a top-down direction by a vertically oriented FIB. Repeating structures of varying density cause curtaining effects because structures of varying density tend to exhibit different mill rates. For example, holes 102, such as through silicon vias (TSV), have a different density than the surrounding silicon substrate. Curtaining is caused due to the difference in mill rates when the FIB is scanned in the area between two holes in a row and when the FIB is scanned over a hole in the same row, essentially milling the row beneath the hole. That is, the FIB passes over either the silicon or the hole at roughly the same point in each scan. This causes positions in the scan with holes to be milled faster than positions in the scan without any holes.

FIG. 8B shows a diagram of a sample cross section with reduced curtaining effects in accordance with embodiments of the present invention. In this example, the cross section was not milled in a top-down direction by a vertically oriented FIB. Instead, the cross section was milled at an angle so that the resultant curtains are spread or aliased across the face of the cross section. That is, as the cross section mill progress from top to bottom, the FIB passes over either silicon or a hole at different points in each scan. In effect, this causes any curtains to spread across the face of the cross section, overlapping one another. The proper angle depends on the geometry of the features in the cross section.

Reducing curtaining in accordance with embodiments of the present invention includes identifying the varying-density structures that will cause problematic curtaining effects, analyzing the geometry of the structures, and offsetting the milling angle to optimize the aliasing effects of spreading the curtains across the structures. Some embodiments of the method include determining a plane through the work piece that maximizes the area of structures that cause curtaining or other image artifacts, tiling the sample so that the plane is normal to the axis of a focused ion beam, and milling the work piece with the focused ion beam to expose a cross section below the plane.

Unlike some methods of minimizing curtaining by adjusting the milling angle, embodiments of the present invention allow for true flat surface viewing of the sample. The full depth cross section of the high aspect ratio interconnect can be viewed at 90 degrees to the SEM with minimal curtaining. The interconnect hole from the top to the bottom can also be viewed 90 degrees to the SEM with minimal curtaining. Some embodiments of the present invention solve the problem of not being able to take a 90 degree viewing angle image of a structure.

Some embodiments permit a user to extract a sample and mount to another positioning system that allows huge flexibility so one can now FIB cross section in directions that were previously not easily performed in chamber. With new positioning, it allows a sample to be optimally positioned for milling to minimize the curtaining effects that cause metrology issues. After milling the sample can then be repositioned at 90 degrees to the SEM at short working distance to get high resolution images of the ROI that had typically been blocked or distorted by curtaining effects.

Figure 9:
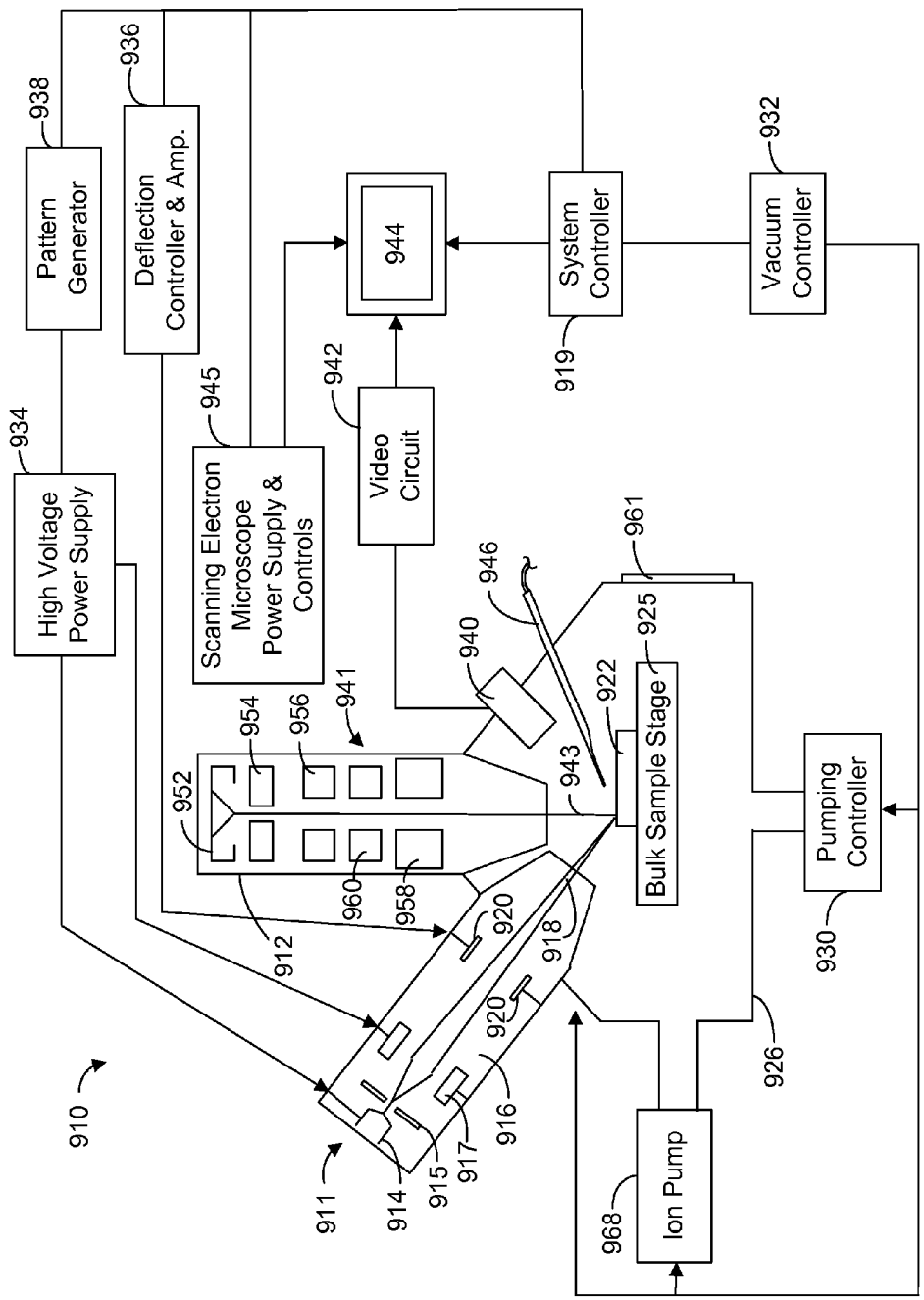
FIG. 9 shows a typical dual beam system 910 suitable for practicing embodiments of the present invention.

FIG. 9 shows a typical dual beam system 910 suitable for practicing embodiments of the present invention, with a vertically mounted SEM column and a FIB column mounted at an angle of approximately 52° from the vertical. Suitable dual beam systems are commercially available, for example, from FEI Company, Hillsboro, Oregon, the assignee of the present application. While an example of suitable hardware is provided below, the invention is not limited to being implemented in any particular type of hardware.

A scanning electron microscope 941, along with power supply and control unit 945, is provided with the dual beam system 910. An electron beam 943 is emitted from a cathode 952 by applying voltage between cathode 952 and an anode 954. Electron beam 943 is focused to a fine spot by means of a condensing lens 956 and an objective lens 958. Electron beam 943 is scanned two-dimensionally on the specimen by means of a deflection coil 960. Operation of condensing lens 956, objective lens 958, and deflection coil 960 is controlled by power supply and control unit 945.

Electron beam 943 can be focused onto substrate 922, which is on movable X-Y stage 925 within lower chamber 926. When the electrons in the electron beam strike substrate 922, secondary electrons are emitted. These secondary electrons are detected by a secondary electron detector 940 as discussed below.

Dual beam system 910 also includes focused ion beam (FIB) system 911 which comprises an evacuated chamber having an upper neck portion 912 within which are located an ion source 914 and a focusing column 916 including extractor electrodes and an electrostatic optical system. The axis of focusing column 916 is tilted 52 degrees from the axis of the electron column. The upper neck portion 912 includes an ion source 914, an extraction electrode 915, a focusing element 917, deflection elements 920, and a focused ion beam 918. Ion beam 918 passes from ion source 914 through focusing column 916 and between electrostatic deflection means schematically indicated at 920 toward substrate 922, which comprises, for example, a semiconductor device positioned on movable X-Y stage 925 within lower chamber 926.

Stage 925 can preferably move in a horizontal plane (X and Y axes) and vertically (Z axis). Stage 925 can also tilt approximately 60° and rotate about the Z axis. A door 961 is opened for inserting substrate 922 onto X-Y stage 925 and also for servicing an internal gas supply reservoir, if one is used. The door is interlocked so that it cannot be opened if the system is under vacuum. Alternative embodiments are described with respect to FIG. 10, in which the charged particle beam system has a motion stage disposed on the bulk sample stage 925.

An ion pump 968 is employed for evacuating upper neck portion 912. The chamber 926 is evacuated with turbomolecular and mechanical pumping system 930 under the control of vacuum controller 932. The vacuum system provides within chamber 926 a vacuum of between approximately $1 \times 10^{-7}$ Torr and $5 \times 10^{-4}$ Torr. If an etch-assisting gas, an etch-retarding gas, or a deposition precursor gas is used, the chamber background pressure may rise, typically to about $1 \times 10^{-5}$ Torr.

The high voltage power supply provides an appropriate acceleration voltage to electrodes in ion beam focusing column focusing 916 for energizing and focusing ion beam 918. When it strikes substrate 922, material is sputtered, that is physically ejected, from the sample. Alternatively, ion beam 918 can decompose a precursor gas to deposit a material.

High voltage power supply 934 is connected to liquid metal ion source 914 as well as to appropriate electrodes in ion beam focusing column 916 for forming an approximately 1 keV to 60 keV ion beam 918 and directing the same toward a sample. Deflection controller and amplifier 936, operated in accordance with a prescribed pattern provided by pattern generator 938, is coupled to deflection plates 920 whereby ion beam 918 may be controlled manually or automatically to trace out a corresponding pattern on the upper surface of substrate 922. In some systems the deflection plates are placed before the final lens, as is well known in the art. Beam blanking electrodes (not shown) within ion beam focusing column 916 cause ion beam 918 to impact onto blanking aperture (not shown) instead of substrate 922 when a blanking controller (not shown) applies a blanking voltage to the blanking electrode.

The liquid metal ion source 914 typically provides a metal ion beam of gallium. The source typically is capable of being focused into a sub one-tenth micrometer wide beam at substrate 922 for either modifying the substrate 922 by ion milling, enhanced etch, material deposition, or for the purpose of imaging the substrate 922.

A charged particle detector 940, such as an Everhart-Thornley detector or multi-channel plate, used for detecting secondary ion or electron emission is connected to a video circuit 942 that supplies drive signals to video monitor 944 and receives deflection signals from controller 919. The location of charged particle detector 940 within lower chamber 926 can vary in different embodiments. For example, a charged particle detector 940 can be coaxial with the ion beam and include a hole for allowing the ion beam to pass. In other embodiments, secondary particles can be collected through a final lens and then diverted off axis for collection.

A gas delivery system 946 extends into lower chamber 926 for introducing and directing a gaseous vapor toward substrate 922. U.S. Pat. No. 5,851,413, to Casella et al. for "Gas Delivery Systems for Particle Beam Processing," assigned to the assignee of the present invention, describes a suitable gas delivery system 946. Another gas delivery system is described in U.S. Pat. No. 5,435,850, to Rasmussen for a "Gas Injection System," also assigned to the assignee of the present invention. For example, a metal organic compound can be delivered to the beam impact point to deposit a metal upon impact of the ion beam or the electron beam. A precursor gas, such as $(CH_3)_3Pt(C_pCH_3)$ to deposit platinum or tungsten hexcarbonyl to deposit tungsten, can be delivered to be decomposed by the electron beam to provide the protective layer in step 108.

A system controller 919 controls the operations of the various parts of dual beam system 910. Through system controller 919, a user can cause ion beam 918 or electron beam 943 to be scanned in a desired manner through commands entered into a conventional user interface (not shown). Alternatively, system controller 919 may control dual beam system 910 in accordance with programmed instructions. A preferred controller is in communication with or includes a memory that stores instructions for automatically carrying out the steps of FIG. 1. In some embodiments, dual beam system 910 incorporates image recognition software, such as software commercially available from Cognex Corporation, Natick, Mass., to automatically identify regions of interest, and then the system can manually or automatically expose cross sections for imaging in accordance with the invention. For example, the system could automatically locate similar features on semiconductor wafers including multiple devices, and expose and form images of features of interest on different (or the same) devices.

In some embodiments of the present invention, the charged particle beam system has a motion stage disposed on the bulk sample stage 925. The bulk sample stage can translate in at least the x-plane and a y-plane. The motion stage can translate independently in the z-plane and rotate along an axis. Using a motion stage on top of bulk stage, a user can view almost all positions and directions by milling and viewing into a volume. A sample is removed from a bulk sample and strategically placed onto the motion stage. If mounted correctly, using the bulk stage in combination with the motion stage, a sample can be positioned to any location and in any orientation the user desires. This can all be accomplished with a single weld method, without venting system or needing a load lock exchange.

Sides of a sample can be viewed from almost all possible angles. An operator wanting real three-dimensional information of a sample can use this method to mill and view anywhere within a sample. The sample can be positioned at short working distance and perpendicular to an electron beam of an electron microscope to obtain high resolution images. A charged particle beam system having a motion stage mounted on a bulk sample stage in accordance with embodiments of the present invention has higher throughput, faster cycle times, and produces a better quality end result.

A single chunk containing the multiple regions of interest is extracted from bulk sample material. The extracted chunk is mounted to a sample holder on an independent motion stage. The sample holder is preferably a needle type sample holder. The independent motion stage allows sample to milled and view simultaneously from almost any direction. The sample can then also be viewed at 90 degrees and at a shorter working distance to the electron beam for high resolution characterization. Multi-plane sample access with a single weld and independent motion opens up many possibilities for users to explore the "dimensions" of their samples. The user can cross section from one direction to locate region of interest, and then plan view cut from the top to characterize it from a completely different direction.

Figure 10:
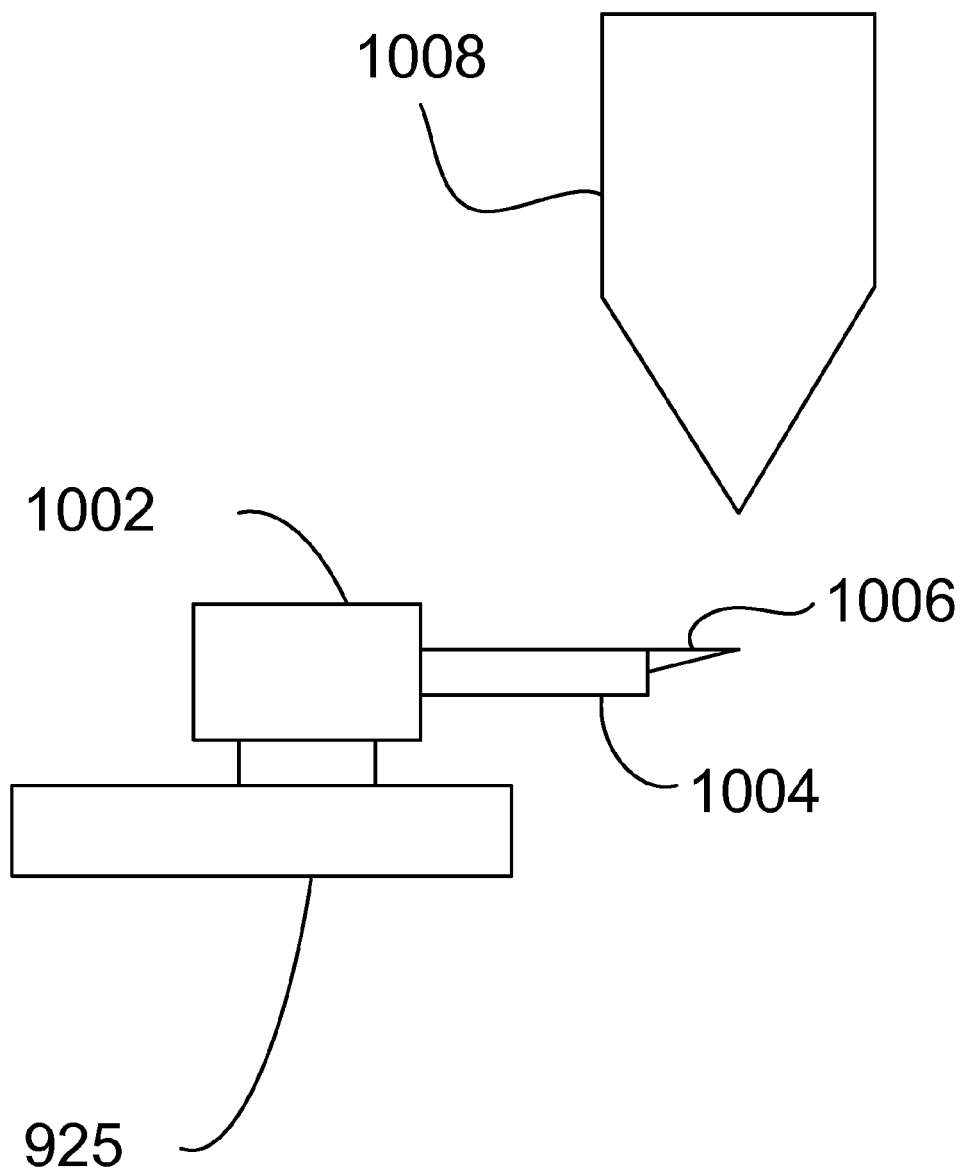
FIG. 10 shows an embodiment of independent motion stage 1002 disposed on a bulk sample stage 925 of a charged particle beam system.

FIG. 10 shows an embodiment of independent motion stage 1002 disposed on a bulk sample stage 925 of a charged particle beam system. Bulk sample stage 925 translates in the x-direction (left to right in FIG. 10) and y-direction (into and out of the paper in FIG. 10). Motion stage 1002 is mounted on bulk sample stage 902. Motion stage 1002 can independently translate in the z-direction (up and down in FIG. 10) and rotate about an axis that is substantially normal to the surface of bulk sample stage 925 to which motion stage 1002 is mounted. Motion stage 1002 includes sample probe 1004. Sample probe 1004 can rotate about its long axis. In one embodiment, sample probe 1004 rotates about an axis that is substantially orthogonal to the axis about which motion stage 1002 rotates. The extracted sample chunk is mounted to a stage-mounted needle 1006 disposed on the end of sample probe 1004. The motion of bulk sample stage 925 and motion stage 1002 can position a sample attached to stage-mounted needle 1006 in nearly any desired orientation with respect to charged particle beam focusing column 1008. Charged particle beam focusing column 1008 can be the focusing column of SEM 941 or FIB 911.

Figure 11:
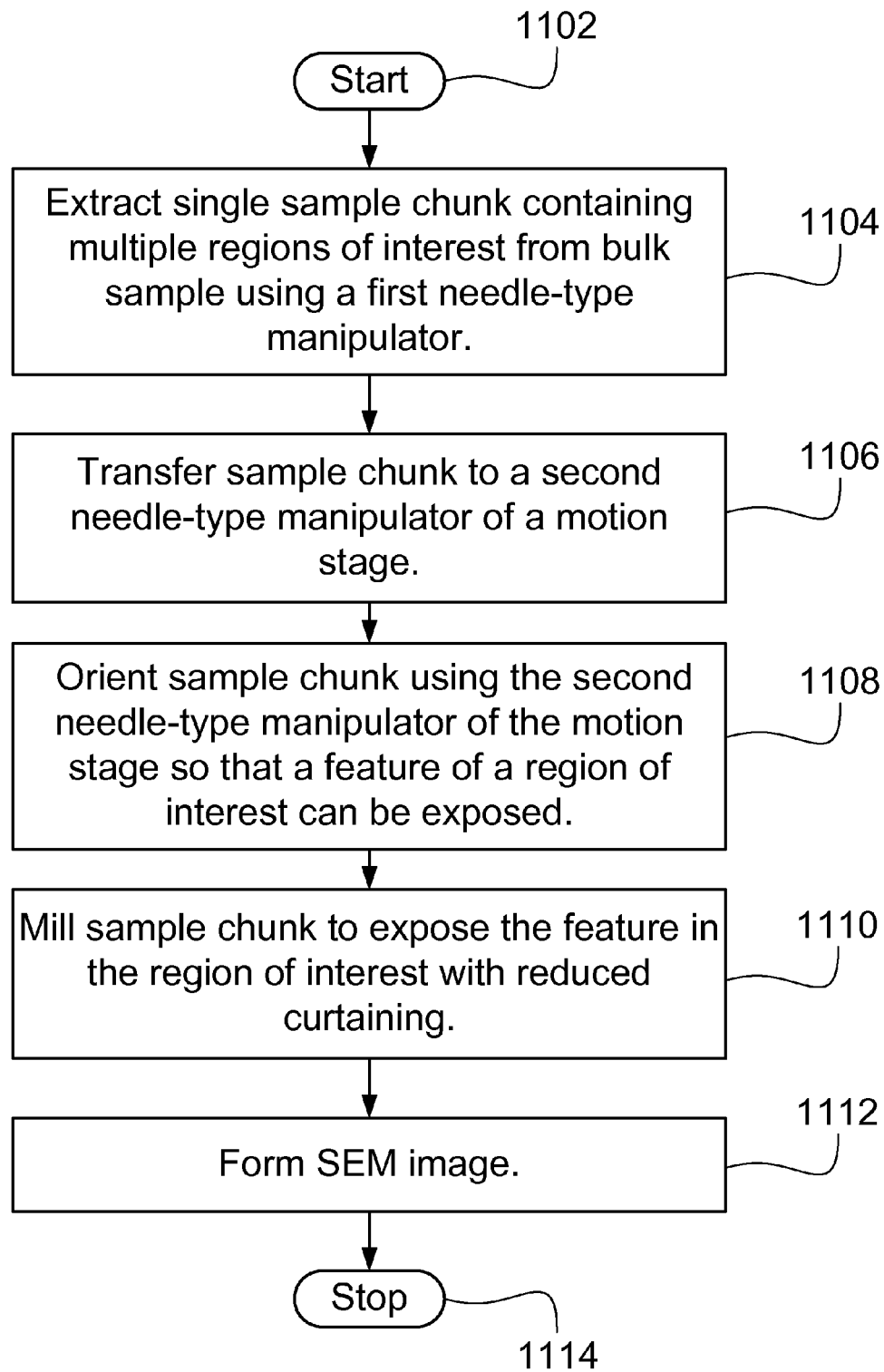
FIG. 11 is a flow chart showing a general process flow of an embodiment of the invention in which a sample chunk having multiple regions of interest is extracted from a sample with a needle-type manipulator, mounted to a second needle-type manipulator on a motion stage, repositioned, and milled before an SEM image is formed of a feature within a region of interest.

FIG. 11 is a flow chart showing a general process flow of an embodiment of the invention in which a sample chunk having multiple regions of interest is extracted from a sample with a needle-type manipulator, mounted to a second needle-type manipulator on a motion stage, repositioned, and milled before an SEM image is formed of a feature within a region of interest. The process begins at step 1102. At step 1104, a single sample chunk containing multiple regions of interest is extracted from bulk sample using a first needle-type manipulator for extraction, such as the EasyLift™ micromanipulator found in charged particle beam systems from FEI Company, the assignee of the present application. At step 1106, the sample chunk is transferred to stage mounted needle 1006 on sample probe 1004 of motion stage 1002. At step 1108, the sample chunk is oriented using the stage mounted needle 1006 so that a feature of at least one of the regions of interest can be exposed by charged particle beam milling. At step 1110, the charged particle beam mills the sample chunk to expose the feature in the region of interest with reduced curtaining. At step 1112, an SEM image is formed of the exposed feature. At step 1114, the process ends.

The present invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

According to some embodiments, a method of exposing a portion of a structure in a sample for observation in a charged particle beam system, comprising extracting a sample from a bulk sample; determining an orientation of the sample that reduces curtaining; mounting the sample to a holder in the charged particle beam system so that the holder orients the sample in an orientation that reduces curtaining when the sample is milled to expose the structure; exposing the structure by milling the sample in a direction that reduces curtaining; and imaging the structure.

In some embodiments, the method in which milling the structure in a direction that reduces curtaining includes rotating the holder.

In some embodiments, the method in which extracting a structure from a bulk sample includes extracting the structure from the bulk sample using a nanomanipulator or other apparatus that has the ability to rotate the sample around at least one axis of rotation.

In some embodiments, the method in which the structure is a high aspect ratio structure.

In some embodiments, the method in which milling the structure includes milling the structure with an ion beam or an electron beam.

In some embodiments, the method in which an image of the structure includes viewing the structure in the image normal to the orientation plane of the structure.

According to some embodiments, a method of exposing a portion of a structure for observation, comprising determining a plane through the work piece that maximizes the area of structures that cause curtaining or other image artifacts; tilting the sample so that the plane is normal to the axis of a focused ion beam; and milling the work piece with the focused ion beam to expose a cross section below the plane.

In some embodiments, the method in which the structures that cause curtaining comprise high aspect ratio holes.

In some embodiments, the method in which the structures that cause curtaining comprise metal structures.

According to some embodiments, a charged particle beam system comprising one or more charged particle beam columns; a bulk sample stage, the bulk sample stage being capable of translating in at least a first direction and a second direction; a motion stage, the motion stage being disposed upon the bulk sample stage, the motion stage being capable of independently translating in a third direction and independently rotating about an axis.

In some embodiments, the charged particle beam system further comprising a sample probe disposed on the motion stage, the sample probe being capable of holding a sample for processing or imaging by the charged particle beam, the sample probe being capable of independently rotating about an axis.

In some embodiments, the charged particle beam system further comprising a controller programmed for extracting a sample from a bulk sample; determining an orientation of the sample that reduces curtaining; mounting the sample to the sample probe; orienting the sample in an orientation that reduces curtaining when the sample is milled to expose a structure in the sample for observation; exposing the structure by milling the sample in a direction that reduces curtaining; and imaging the structure.

In some embodiments, the charged particle beam system further comprising a controller programmed for extracting a sample from a bulk sample; mounting the sample to the sample probe; determining a plane through the work piece that maximizes the area of structures that cause curtaining or other image artifacts; tilting the sample so that the plane is normal to the axis of a focused ion beam; and milling the work piece with the focused ion beam to expose a cross section below the plane.

In some embodiments, the charged particle beam system further comprising a nanomanipulator for extracting a sample from a bulk sample.

In some embodiments, the charged particle beam system in which the nanomanipulator is adapted for transferring the sample from the bulk sample to the sample probe.

In some embodiments, the charged particle beam system in which the structure is a high aspect ratio structure.

In some embodiments, the charged particle beam system in which the one or more charged particle beam columns is an ion beam column or an electron beam column In some embodiments, the charged particle beam system in which the structure is a high aspect ratio structure.

In some embodiments, the charged particle beam system in which the one or more charged particle beam columns is an ion beam column or an electron beam column.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of exposing a portion of a structure in a sample for observation in a charged particle beam system, comprising:
   extracting a sample from a bulk sample;
   determining an orientation of the sample that reduces curtaining among a plurality of high aspect ratio structures;
   mounting the sample to a holder in the charged particle beam system so that the holder orients the sample in an orientation that reduces curtaining when the sample is milled to expose the structure;
   exposing the structure by milling the sample in a direction that reduces curtaining; and
   imaging the structure.

2. The method of claim 1 in which milling the structure in a direction that reduces curtaining includes rotating the holder.

3. The method of claim 1 in which extracting a structure from a bulk sample includes extracting the structure from the bulk sample using a nanomanipulator or other apparatus that has the ability to rotate the sample around at least one axis of rotation.

4. The method of claim 1 in which the high aspect ratio structures comprise high aspect ratio holes.

5. The method of claim 1 in which milling the structure includes milling the structure with an ion beam or an electron beam.

6. The method of any of claim 1 in which an image of the structure includes viewing the structure in the image normal to the orientation plane of the structure.

7. A method of exposing a portion of a structure for observation, comprising:
   determining a plane through the work piece that maximizes the area of structures that cause curtaining or other image artifacts;
   tilting the sample so that the plane is normal to the axis of a focused ion beam; and
   milling the work piece with the focused ion beam to expose a cross section below the plane.

8. The method of claim 7 in which the structures that cause curtaining comprise high aspect ratio holes.

9. The method of claim 7 in which the structures that cause curtaining comprise metal structures.

10. A charged particle beam system comprising:
    one or more charged particle beam columns;
    a bulk sample stage, the bulk sample stage being capable of translating in at least a first direction and a second direction;
    a motion stage, the motion stage being disposed upon the bulk sample stage, the motion stage being capable of independently translating in a third direction and independently rotating about an axis.

11. The charged particle beam system of claim 10, further comprising:
    a sample probe disposed on the motion stage, the sample probe being capable of holding a sample for processing or imaging by the charged particle beam, the sample probe being capable of independently rotating about an axis.

12. The charged particle beam system of claim 11, further comprising a controller programmed for:
    extracting a sample from a bulk sample;
    determining an orientation of the sample that reduces curtaining;
    mounting the sample to the sample probe;
    orienting the sample in an orientation that reduces curtaining when the sample is milled to expose a structure in the sample for observation;
    exposing the structure by milling the sample in a direction that reduces curtaining; and
    imaging the structure.

13. The charged particle beam system of claim 12, further comprising a nanomanipulator for extracting a sample from a bulk sample.

14. The charged particle beam system of claim 13, in which the nanomanipulator is adapted for transferring the sample from the bulk sample to the sample probe.

15. The charged particle beam system of claim 12 in which the structure is a high aspect ratio structure.

16. The charged particle beam system of claim 12 in which the one or more charged particle beam columns is an ion beam column or an electron beam column.

17. The charged particle beam system of any of claim 12 in which the structure is a high aspect ratio structure.

18. The charged particle beam system of any of claim 12 in which the one or more charged particle beam columns is an ion beam column or an electron beam column.

19. The charged particle beam system of claim 11, further comprising a controller programmed for:
   extracting a sample from a bulk sample;
   mounting the sample to the sample probe;
   determining a plane through the work piece that maximizes the area of structures that cause curtaining or other image artifacts;
   tilting the sample so that the plane is normal to the axis of a focused ion beam; and
   milling the work piece with the focused ion beam to expose a cross section below the plane.

* * * * *